US00PP22374P2

(12) United States Plant Patent
Smith

(10) Patent No.: US PP22,374 P2
(45) Date of Patent: Dec. 20, 2011

(54) ***PAEONIA* PLANT NAMED 'SMITH OPUS 2'**

(50) Latin Name: ***Paeonia lactiflora*×[(*Paeonia lutea*×*Paeonia suffruticosa*)×*Paeonia rockii*]**
Varietal Denomination: Smith Opus 2

(76) Inventor: Donald Robert Smith, W. Newton, MA (US)

( * ) Notice: Subject to any disclaimer, the term of this patent is extended or adjusted under 35 U.S.C. 154(b) by 0 days.

(21) Appl. No.: 12/807,627

(22) Filed: Sep. 9, 2010

(51) Int. Cl.
*A01H 5/00* (2006.01)

(52) U.S. Cl. ..... Plt./316

(58) Field of Classification Search ..... Plt./316
See application file for complete search history.

(56) References Cited

U.S. PATENT DOCUMENTS

PP4,233 P * 4/1978 Klehm ..... Plt./316
PP5,718 P * 4/1986 Hollingsworth ..... Plt./316
PP19,374 P2 * 10/2008 Smith ..... Plt./316

* cited by examiner

*Primary Examiner* — Wendy C Haas
(74) *Attorney, Agent, or Firm* — C. A. Whealy

(57) ABSTRACT

A new and distinct cultivar of *Paeonia* plant named 'Smith Opus 2', characterized by its compact and symmetrically globular plant habit; vigorous growth habit; relatively narrow and finely-incised leaves; numerous large flowers that are arranged on strong peduncles above and beyond the foliar plane; long flowering period; flowers with creamy white-colored petals with purple-colored margins and large prominent red purple-colored flares at the petal bases; and good garden performance.

2 Drawing Sheets

Botanical designation: *Paeonia lactiflora*×[(*Paeonia lutea*×*Paeonia suffruticosa*)×*Paeonia rockii*].
Cultivar denomination: 'SMITH OPUS 2'.

BACKGROUND OF THE INVENTION

The present invention relates to a new and distinct cultivar of *Paeonia* plant, botanically known as *Paeonia lactiflora*×[(*Paeonia lutea*×*Paeonia suffruticosa*)×*Paeonia rockii*] and hereinafter referred to by the name 'Smith Opus 2'.

The new *Paeonia* plant is a product of a planned breeding program conducted by the Inventor in West Newton, Mass. and Windham, N.H. The objective of the breeding program is to create new hardy *Paeonia* plants with unique and attractive flower coloration.

The new *Paeonia* plant originated from a cross-pollination in 1998 in West Newton, Mass. of *Paeonia lactiflora* 'Martha W.', not patented, as the female, or seed, parent with [(*Paeonia lutea*×*Paeonia suffruticosa*)×*Paeonia rockii*] 'D-67', not patented, as the male, or pollen, parent. The new *Paeonia* plant was discovered in June, 2004 and selected in 2005 by the Inventor as a single flowering plant from within the progeny of the stated cross-pollination in a controlled environment in Windham, N.H.

Asexual reproduction of the new *Paeonia* plant by tissue culture in Chicoutimi, Canada, since April, 2005, has shown that the unique features of this new *Paeonia* plant are stable and reproduced true to type in successive generations.

SUMMARY OF THE INVENTION

Plants of the new *Paeonia* have not been observed under all possible environmental conditions. The phenotype may vary somewhat with variations in environment such as temperature and light intensity without, however, any variance in genotype.

The following traits have been repeatedly observed and are determined to be the unique characteristics of 'Smith Opus 2'. These characteristics in combination distinguish 'Smith Opus 2' as a new and distinct *Paeonia* plant:

1. Compact and symmetrically globular plant habit.
2. Vigorous growth habit.
3. Relatively narrow and finely-incised leaves.
4. Numerous large flowers that are arranged on strong peduncles above and beyond the foliar plane.
5. Long flowering period.
6. Flowers with creamy white-colored petals with purple-colored margins and large prominent red purple-colored flares at the petal bases.
7. Good garden performance.

Plants of the new *Paeonia* differ primarily from plants of the female parent, 'Martha W.', in the following characteristics:

1. Plants of the new *Paeonia* are more compact than and not as upright as plants of 'Martha W.'.
2. Plants of the new *Paeonia* have more finely-incised leaves than plants of 'Martha W.'.
3. Plants of the new *Paeonia* have larger flowers than plants of 'Martha W.'.
4. Plants of the new *Paeonia* and 'Martha W.' differ in flower color as plants of 'Martha W.' have pink-colored flowers.

Plants of the new *Paeonia* differ primarily from plants of the male parent, 'D-67', in the following characteristics:

1. Plants of the new *Paeonia* are more compact than plants of 'D-67'.
2. Plants of the new *Paeonia* are more freely branching than plants of 'D-67'.
3. Plants of the new *Paeonia* have more finely-incised leaves than plants of 'D-67'.
4. Plants of the new *Paeonia* have larger flowers than plants of 'D-67'.

5. Flowers of plants of the new *Paeonia* and 'D-67' differ in flower color as plants of 'D-67' have yellow-colored flowers with large red-colored central flares.

Plants of the new *Paeonia* can be compared to plants of *Paeonia* 'Garden Treasure', disclosed in U.S. Plant Pat. No. 5,718. In side-by-side comparisons conducted by the Inventor in Windham, N.H., plants of the new *Paeonia* differed from plants of 'Garden Treasure' in the following characteristics:

1. Plants of the new *Paeonia* were larger and more upright than plants of 'Garden Treasure'.
2. Plants of the new *Paeonia* were more freely branching than plants of 'Garden Treasure'.
3. Plants of the new *Paeonia* had more finely-incised leaves than plants of 'Garden Treasure'.
4. Plants of the new *Paeonia* flowered earlier and were more freely flowering than plants of 'Garden Treasure'.
5. Flowers of plants of the new *Paeonia* had fewer petals than flowers of plants of 'Garden Treasure'.
6. Plants of the new *Paeonia* and 'Garden Treasure' differed in flower color as plants of 'Garden Treasure' had yellow-colored flowers without central flares.

Plants of the new *Paeonia* can also be compared to plants of *Paeonia* 'Singing In The Rain II', disclosed in U.S. Plant Pat. No. 19,374. In side-by-side comparisons conducted by the Inventor in Windham, N.H., plants of the new *Paeonia* differed from plants of 'Singing In The Rain II' in the following characteristics:

1. Plants of the new *Paeonia* were taller than and not as compact as plants of 'Singing In The Rain II'.
2. Plants of the new *Paeonia* were more outwardly spreading than and not as upright as 'Singing In The Rain II'.
3. Plants of the new *Paeonia* had larger flowers with fewer petals than plants of 'Singing In The Rain II'.
4. Flowers of plants of the new *Paeonia* and 'Singing In The Rain II' differed in flower color as flowers of plants of 'Singing In The Rain II' were bright yellow in color without central flares.

BRIEF DESCRIPTION OF THE PHOTOGRAPHS

The accompanying colored photographs illustrate the overall appearance of the new *Paeonia* plant showing the colors as true as it is reasonably possible to obtain in colored reproductions of this type. Colors in the photographs may differ slightly from the color values cited in the detailed botanical description which accurately describe the actual colors of the new *Paeonia* plant.

The photograph on the first sheet comprises a side perspective view of a typical flowering plant of 'Smith Opus 2' grown in an outdoor nursery.

The photograph on the second sheet is a close-up view of a typical opened flower and a typical flower bud of 'Smith Opus 2'.

DETAILED BOTANICAL DESCRIPTION

Plants used for the aforementioned photographs and following description were grown under conditions which closely approximate commercial production conditions during the early spring and summer in an outdoor nursery in Windham, N.H. During the production of the plants, day temperatures ranged from 3° C. to 32° C. and night temperatures ranged from −1° C. to 20° C. Plants were six years old when the photographs and the description were taken. In the following description, color references are made to The Royal Horticultural Society Colour Chart, 2001 Edition, except where general terms of ordinary dictionary significance are used.

Botanical classification: *Paeonia lactiflora*×[(*Paeonia lutea*×*Paeonia suffruticosa*)×*Paeonia rockii*] 'Smith Opus 2'.

Parentage:

*Female, or seed, parent.*—*Paeonia lactiflora* 'Martha W.', not patented.

*Male, or pollen, parent.*—[(*Paeonia lutea*×*Paeonia suffruticosa*)×*Paeonia rockii*] 'D-67', not patented.

Propagation:

*Type.*—By tissue culture.

*Root description.*—Fleshy, thick; close to 166C to 166D in color.

*Rooting habit.*—Freely branching; dense.

Plant description:

*Plant and growth habit.*—Perennial herbaceous subshrub; compact and symmetrically globular plant habit; vigorous growth habit; rapid growth rate.

*Plant height.*—About 76 cm to 86 cm.

*Plant width.*—About 114 cm to 122 cm.

Axillary stem description:

*Quantity per primary branch.*—About two.

*Length.*—About 24 cm.

*Diameter.*—About 4.2 cm.

*Internode length.*—About 10 cm, highly variable.

*Aspect.*—Mostly upright to slightly arching.

*Strength.*—Strong.

*Texture.*—Smooth, glabrous.

*Color.*—Close to 144A.

Foliage description:

*Arrangement.*—Alternate, bi-ternately compound with about nine leaflets per leaf.

*Leaf length.*—About 28 cm.

*Leaf width.*—About 23 cm to 28 cm.

*Leaflet length.*—About 5 cm to 11 cm.

*Leaflet width.*—About 4 cm to 9 cm.

*Leaflet shape.*—Broadly elliptical, finely incised.

*Leaflet apex.*—Broadly acuminate often with emargination.

*Leaflet base.*—Attenuate.

*Leaflet margin.*—Finely and deeply incised.

*Leaflet texture, upper and lower surfaces.*—Smooth, glabrous.

*Leaflet venation pattern.*—Pinnate; reticulate.

*Leaflet color.*—Developing leaves, upper surface: Close to 146C overlain with close to 46A. Developing leaves, lower surface: Close to 147C overlain with close to 46A. Fully expanded leaves, upper surface: Close to 137B; venation, close to 145A. Fully expanded leaves, lower surface: Close to 191A; venation, close to 145A.

*Petiole length.*—About 14 cm.

*Petiole diameter.*—About 6 mm.

*Petiole texture, upper and lower surfaces.*—Smooth, glabrous.

*Petiole color, upper surface.*—Close to 145A to 145B; venation, close to 182B and 181B.

*Petiole color, lower surface.*—Close to 144A; venation, close to 144A.

Flower description:

*Flower shape, arrangement and flowering habit.*—Single cupped flowers; flowers terminal or axillary; flowers face upright to outward; flowers arranged on strong peduncles above and beyond the foliage; freely flowering habit, about 40 to 60 flowers develop per plant.

*Natural flowering season.*—Long flowering period, flowering continuous from late spring to early summer in an outdoor nursery in New Hampshire; plants begin flowering about 60 days after bud break in the early spring.

*Flower longevity.*—Flowers last about six days on the plant and about three days as a cut flower; flowers not persistent.

*Fragrance.*—Mild, lemon-like.

*Flower buds.*—Length: About 3 cm to 3.4 cm. Diameter: About 2.6 cm to 2.8 cm. Shape: Globose with cuspidate apex. Color: Close to 144A to 144B, often flushed with close to 183C to 183D.

*Flowers.*—Diameter: About 15 cm to 18 cm. Depth (height): About 6 cm to 7 cm.

*Petals.*—Quantity and arrangement: About nine to eleven in about two imbricate whorls. Length: About 10 cm. Width: About 8 cm. Shape: Rounded to nearly cordate. Apex: Emarginate with pronounced V-shaped central notch. Margin: Entire, sinuate or lobed. Texture, upper and lower surfaces: Smooth, glabrous. Color: When opening, upper and lower surfaces: Close to N155B to N155D heavily overlain with close to N74C to N74D; small streaks and flecks, close to N74C. Fully opened, upper and lower surfaces: Close to 155B; towards the margins, close to 76A or 77D; base, central flares, close to 59A.

*Sepals.*—Quantity and arrangement: Three in a single whorl. Length: About 2.9 cm. Width: About 3.8 cm. Shape: Obcordate to obovate; cupped. Apex: Mucronate. Base: Truncate. Margin: Entire. Texture, upper and lower surfaces: Smooth, glabrous; leathery. Color, upper surface: Close to 144A and N144B. Color, lower surface: Close to 144A to 144B.

*Peduncles.*—Length: About 74 cm. Diameter, towards the base: About 9 mm to 12 mm. Strength: Strong. Texture: Smooth, glabrous. Color: Close to 144A.

*Reproductive organs.*—Stamens: Quantity per flower: About 50 to 70. Filament length: About 1.3 cm. Filament color: Towards the base, close to 46A; towards the apex, close to 11C. Anther shape: Elongated ovoid. Anther length: About 3 mm to 6 mm. Anther color: Close to 17A. Pollen amount: Scarce. Pollen color: Close to 14A. Pistils: Quantity per flower: About three. Pistil length: About 2.2 cm to 2.5 cm. Stigma shape: Claw-shaped, acutely convex. Stigma color: Close to 11C. Ovary color: Close to 137B.

*Seed/fruit.*—Seed and fruit production has not been observed.

Disease resistance: Plants of the new *Paeonia* have been observed to be resistant to Leaf Spot and Powdery Mildew.

Garden performance: Plants of the new *Paeonia* have good garden performance and have exhibited good tolerance to rain and wind and have been observed to tolerate temperatures from about −30° C. to about 37° C.

It is claimed:

1. A new and distinct *Paeonia* plant named 'Smith Opus 2' as illustrated and described.

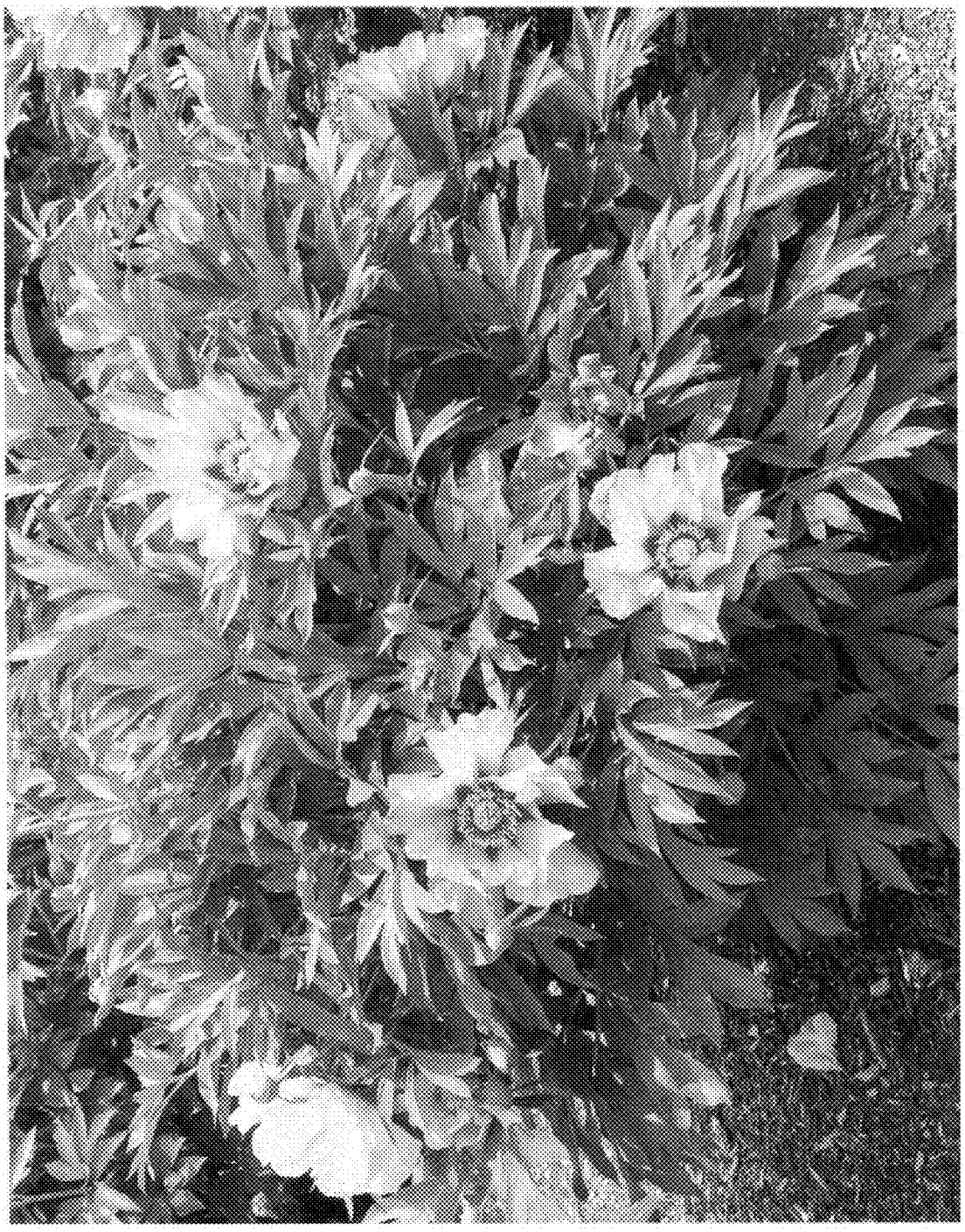

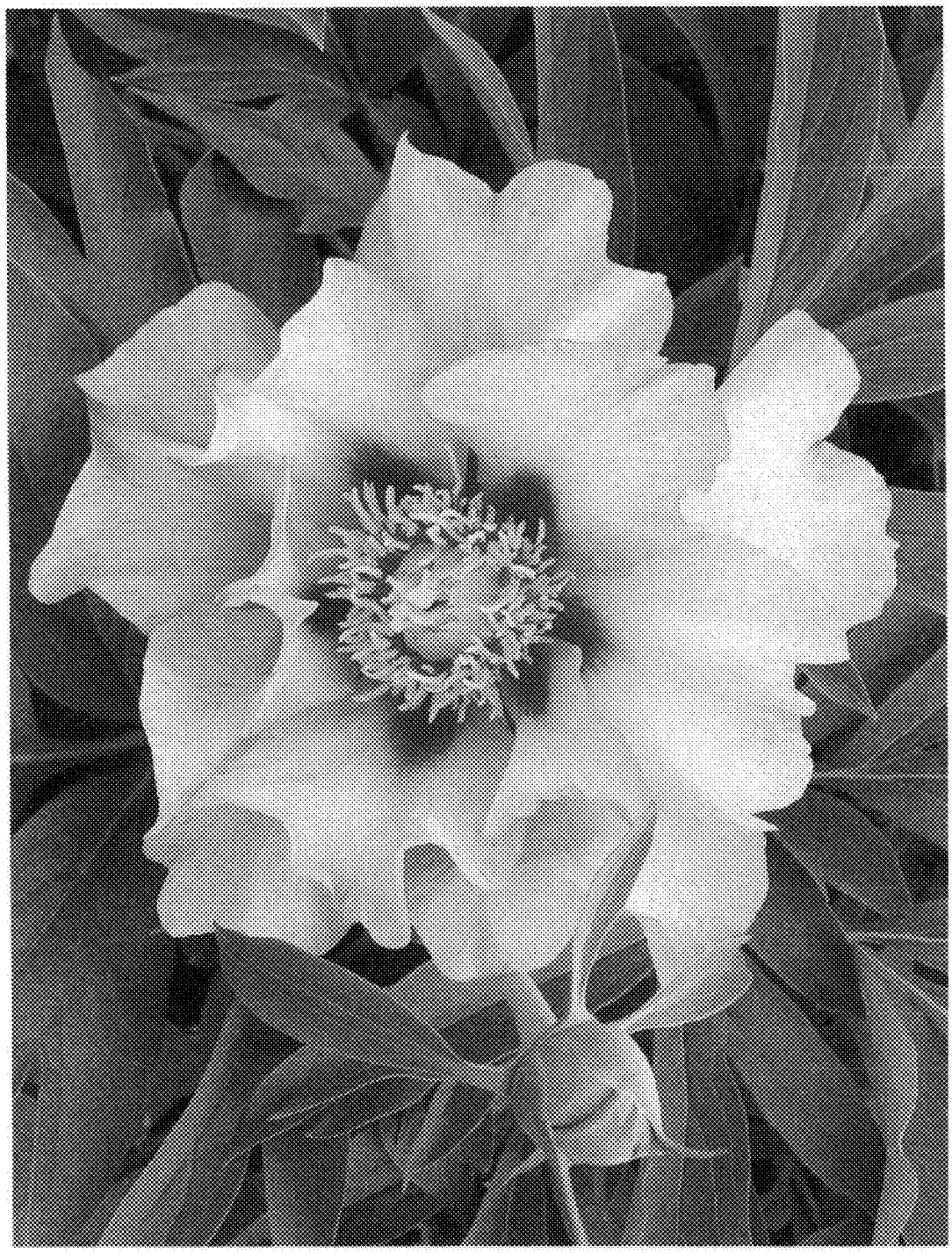

* * * * *